(12) United States Patent
Biedermann et al.

(10) Patent No.: US 8,506,611 B2
(45) Date of Patent: *Aug. 13, 2013

(54) BONE ANCHORING DEVICE

(75) Inventors: Lutz Biedermann, VS-Villingen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/245,361

(22) Filed: Sep. 26, 2011

(65) Prior Publication Data

US 2012/0109224 A1 May 3, 2012

Related U.S. Application Data

(63) Continuation of application No. 12/791,509, filed on Jun. 1, 2010, now Pat. No. 8,048,183, which is a continuation of application No. 11/548,856, filed on Oct. 12, 2006, now Pat. No. 7,749,258.

(60) Provisional application No. 60/726,032, filed on Oct. 12, 2005.

(30) Foreign Application Priority Data

Oct. 12, 2005 (EP) ..................................... 05022263

(51) Int. Cl.
*A61B 17/88* (2006.01)
(52) U.S. Cl.
USPC ........... 606/308; 606/266; 606/267; 606/270; 606/306; 606/305
(58) Field of Classification Search
USPC ........................ 606/265–270, 305–308, 319
See application file for complete search history.

(56) References Cited

U.S. PATENT DOCUMENTS

| 5,005,562 A | 4/1991 | Cotrel |
| 5,181,917 A | 1/1993 | Rogozinski |
| 5,443,467 A | 8/1995 | Biedermann et al. |
| 6,254,602 B1 | 7/2001 | Justis |

(Continued)

FOREIGN PATENT DOCUMENTS

| CN | 1604758 A | 4/2005 |
| EP | 0879579 A2 | 11/1998 |

(Continued)

OTHER PUBLICATIONS

European Search Report for European Application No. 05022263.7-2318 dated Feb. 22, 2006 and mailed Mar. 1, 2006, 6 pp.
Notice of Allowance for parallel KR Application No. 10-2006-0097933, dated May 1, 2013 (2 sheets), and English translation (1 sheet).

*Primary Examiner* — Eduardo C Robert
*Assistant Examiner* — Julianna N Harvey
(74) *Attorney, Agent, or Firm* — Christie, Parker & Hale, LLP

(57) ABSTRACT

A bone anchoring device includes a receiving part for receiving a rod, the receiving part has a first bore coaxial with a longitudinal axis and a second bore, and an anchoring element having a first end for insertion into the bone and a second end positionable within a second bore, the anchoring element being movable relative to the receiving part in limited angular range about the longitudinal axis, the angles lying in a single plane. The bone anchoring device further includes a fixation element cooperating with the receiving part to lock the anchoring element relative to the receiving part. The anchoring element is pivotable relative to the receiving part around one rotational axis transverse to the longitudinal axis.

22 Claims, 7 Drawing Sheets

(56) References Cited

U.S. PATENT DOCUMENTS

| | | |
|---|---|---|
| 6,736,820 B2 | 5/2004 | Biedermann et al. |
| 6,800,079 B2 | 10/2004 | Reed |
| 2006/0155277 A1 | 7/2006 | Metz-Stavenhagen |
| 2006/0200131 A1* | 9/2006 | Chao et al. .................. 606/61 |

FOREIGN PATENT DOCUMENTS

| | | |
|---|---|---|
| JP | 2005-506128 A | 3/2005 |
| WO | WO 03/032863 A2 | 4/2003 |
| WO | WO 2006/096306 A2 | 9/2006 |

* cited by examiner

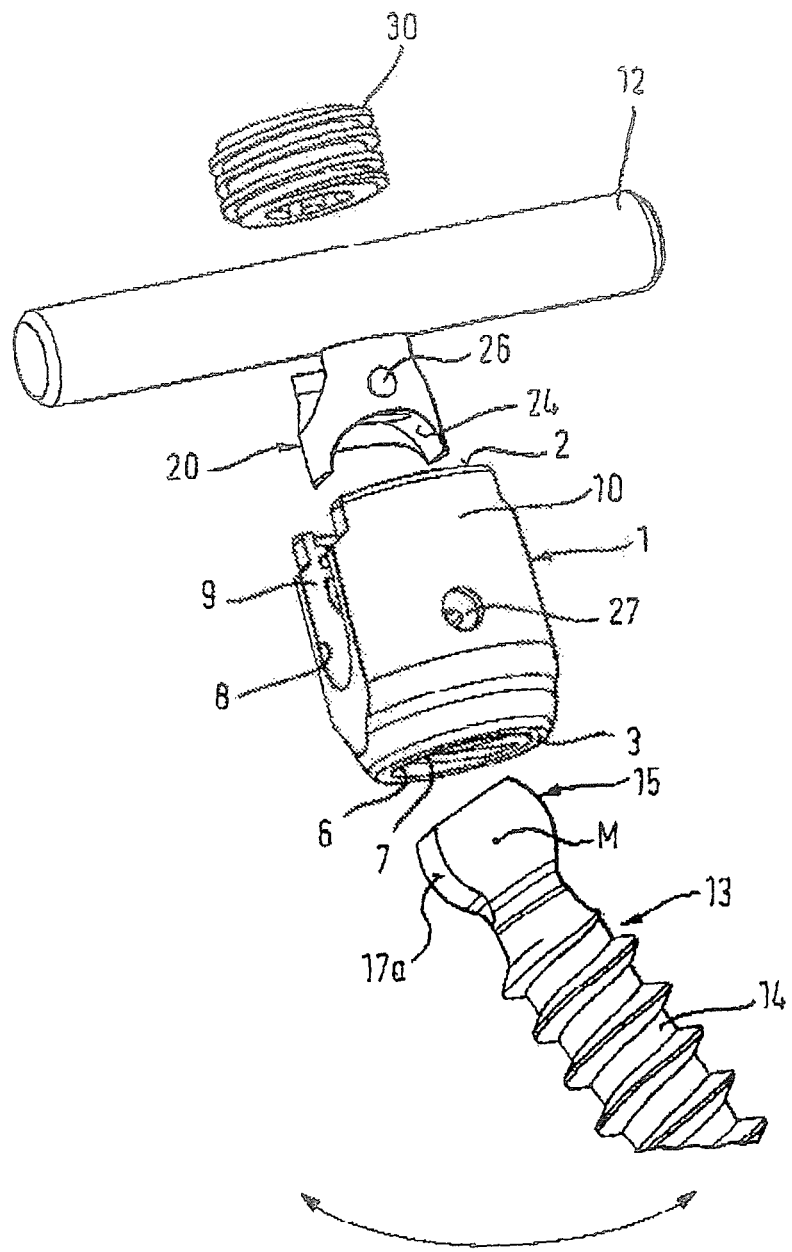

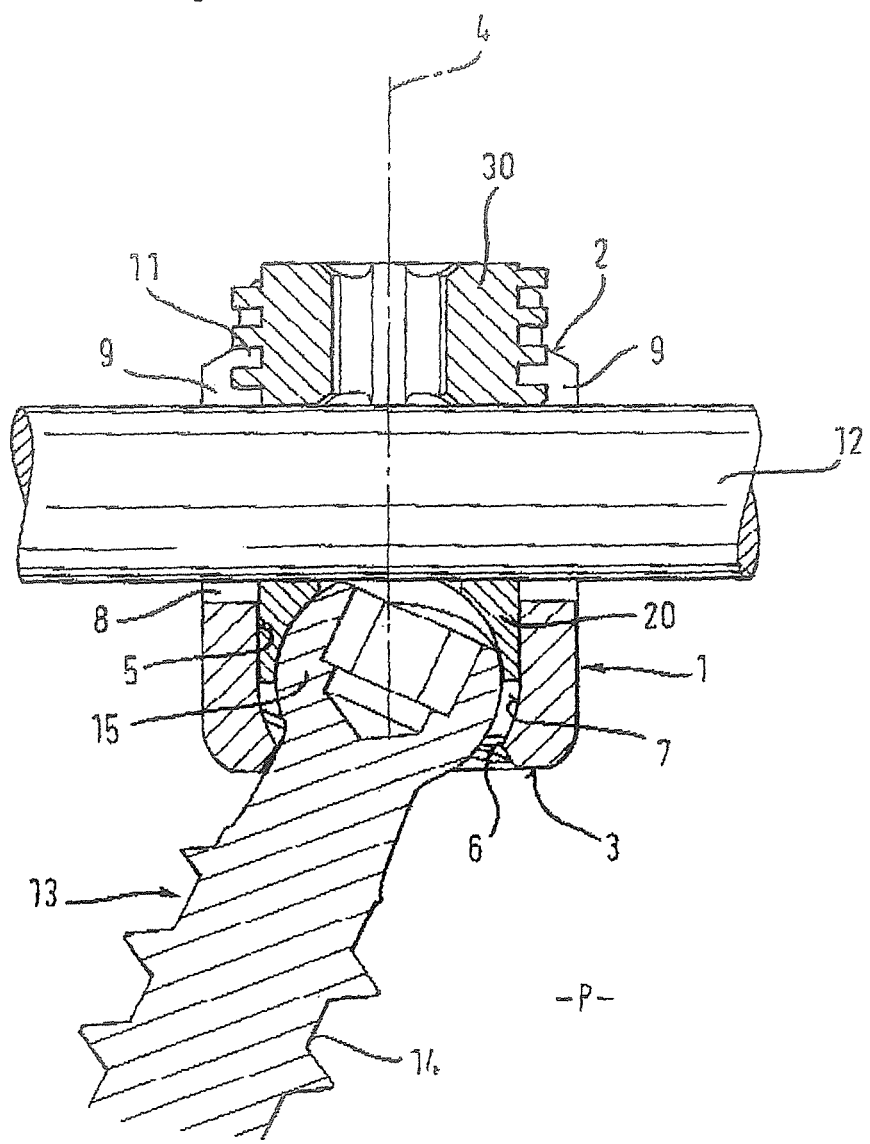

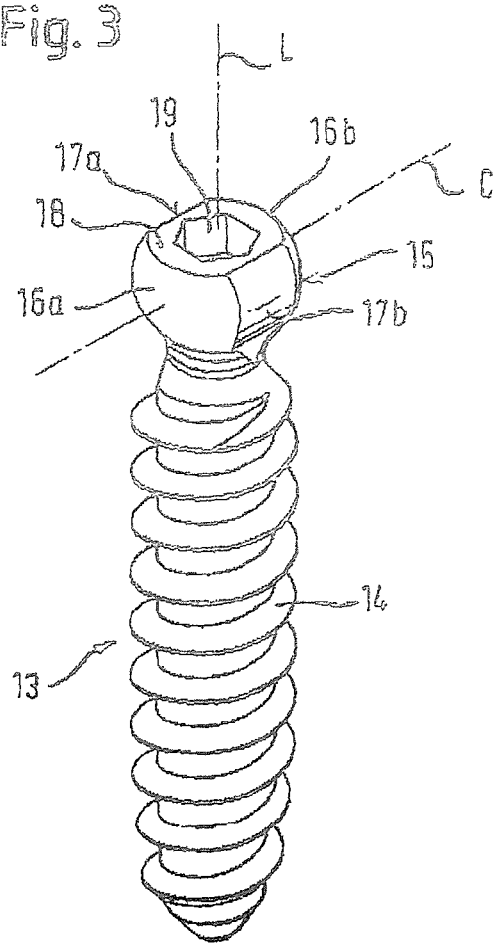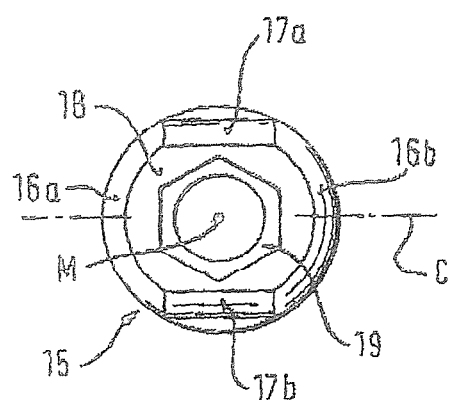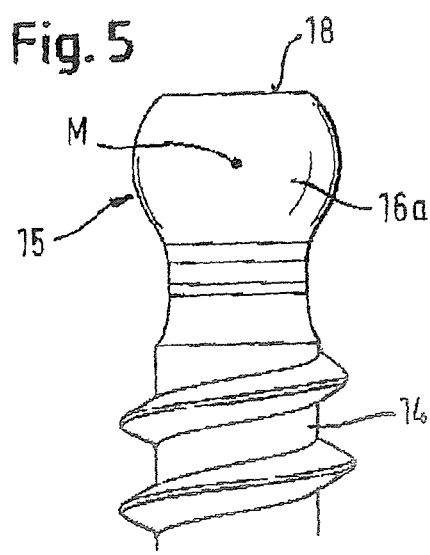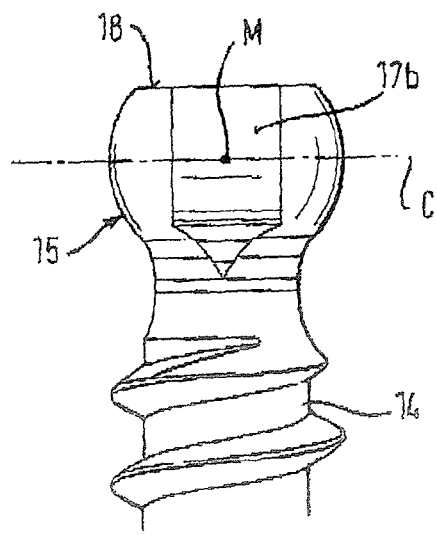

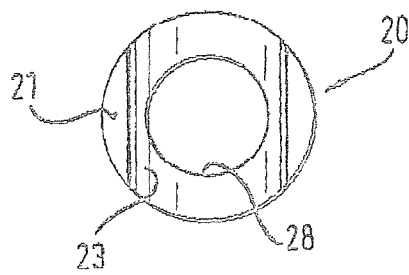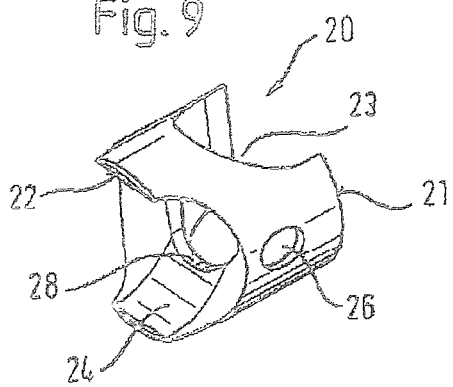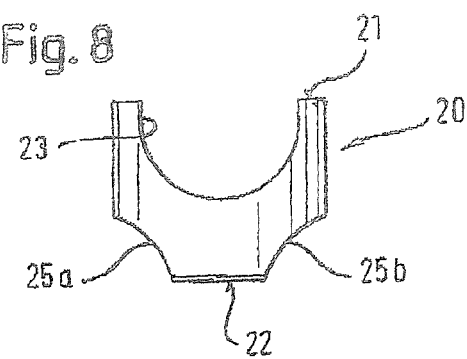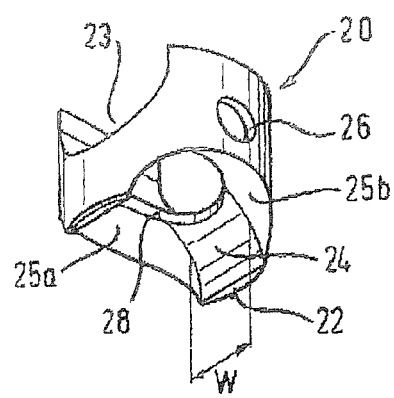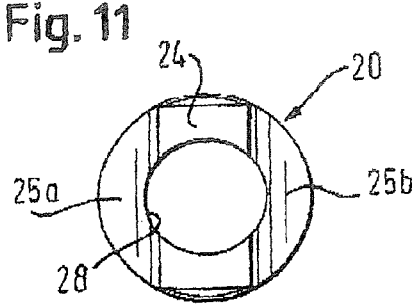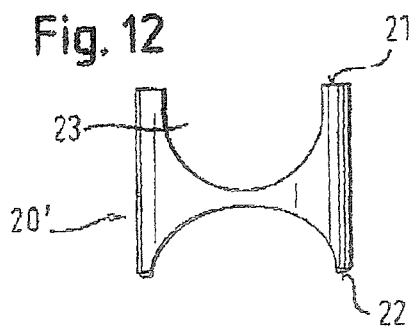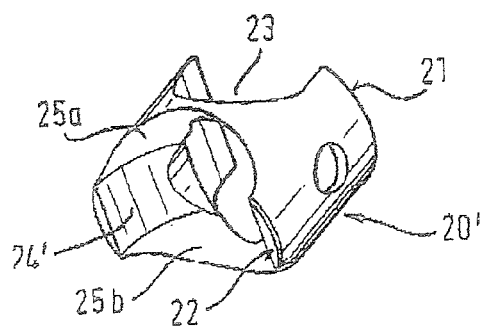

BONE ANCHORING DEVICE

CROSS-REFERENCE TO RELATED APPLICATION(S)

This application is a continuation of application Ser. No. 12/791,509, filed Jun. 1, 2010 now U.S. Pat. No. 8,048,133, which is a continuation of application Ser. No. 11/548,856, filed Oct. 12, 2006, now U.S. Pat. No. 7,749,258, which claims the benefit of U.S. Provisional Patent Application Ser. No. 60/726,032, filed Oct. 12, 2005, and claims priority from European Patent Application EP05022263.7, filed Oct. 12, 2005, the entire disclosures of which are incorporated herein by reference.

BACKGROUND

The present disclosure relates to surgical devices, and more particularly, to a bone anchoring device.

U.S. Pat. No. 5,005,562 discloses a bone anchoring device having a threaded shaft or a hook to be anchored in the bone and a head formed integrally with the shaft, the head having a U-shaped recess for receiving a rod. This so-called monoaxial bone anchoring device has a high resistance to loads. However, the possibility to adjust the position of the head to the anatomical conditions is limited.

U.S. Pat. No. 5,443,467 discloses a bone anchoring device comprising a receiving part for receiving a rod and a bone anchoring element having a threaded shaft and a spherical head which is pivotably held in the receiving part. With this so-called polyaxial bone anchoring element the anchoring member can be pivoted in a range of generally up to about ±25° about the longitudinal axis of the receiving part in directions in a range of 360° around the longitudinal axis. Therefore, it is possible that even after screwing-in the threaded section of the bone anchoring member into the bone the adjustment of the orientation of the receiving part relative to the anchoring element in order to receive the rod is possible. After the orientation of the receiving part has been adjusted to the anatomical conditions and the rod has been inserted into the receiving part, the bone anchoring device is locked.

US 2006/0155277 A1 describes an anchoring element, which comprises a retaining means for receiving a rod, the retaining means having a ring-shaped mount, a fastening element for anchoring the device in the vertebra, and a securing element which can be screwed into a thread of the retaining means in order to fix the fastening element with an angle relative to the retaining means. The fastening element comprises a threaded shank and a bearing, the latter being provided to achieve a pivotal motion when being supported by a separate intermediate element, which can be inserted into the ring-shaped mount of the retaining means. More specifically, the bearing includes spherical surfaces which engage with spherical counterparts of the intermediate element. The bearing further has two flat guiding surfaces formed on opposite sides thereof, which engage with respectively flat counter surfaces of the intermediate element. The fastening element may perform a rotation movement around one single axis with respect to the intermediate element. However, the intermediate element can freely rotate within the mount around a longitudinal axis of the retaining means. Hence, a polyaxial adjustment of the fastening element relative to the retaining means is possible. The final fixation is achieved by screwing the securing element into the thread of the retaining means after the rod is inserted. As a result thereof, pressure is exerted onto the rod, which transmits this pressure further to the intermediate element which then frictionally clamps the bearing. Thus, upon fixation by the securing element, the degree of free movement is reduced from polyaxial to fully rigid at the same time.

For certain clinical applications, for example in the region of the cervical vertebrae, due to the small dimensions of the cervical vertebrae, a greater degree of pivoting to one specific side is necessary than it is the case in the region of the larger thoracic vertebrae and lumbar vertebrae. U.S. Pat. No. 6,736,820 B2 discloses a bone screw having a screw member with a threaded section and a head which is pivotably held in a receiving part receiving a rod. The screw member can be pivoted to at least one side by an enlarged angle. This is accomplished by providing an edge of the receiving part with an asymmetric construction. However, the screw member is still pivotable in all directions in a 360° angular range around its screw axis.

An example of a Cosmic Posterior Dynamic System is shown in FIG. 17 that includes a bone anchoring device having a receiving part 100 receiving a rod 101 and a bone screw 102, wherein the bone screw is pivotably held in the receiving part around a pivot axis 103 formed by a transverse pin 105 which is perpendicular to the longitudinal axis 104 of the receiving part and perpendicular to the rod. Hence, the bone screw can be pivoted in a single plane containing the longitudinal axis of the receiving part. The position of the bone screw relative to the receiving part cannot be locked and therefore, the bone screw and the receiving part are movable relative to each other all the time.

In view of the above, there is a need for a bone anchoring device which can be adjustable, which can have an improved load resistance, can be easy to handle and safe to lock the angled position of the bone screw.

SUMMARY

A bone anchoring device according to the present disclosure includes an anchoring element to be anchored in the bone and a receiving part for receiving a rod to be connected to the anchoring element, wherein the receiving part has a first bore coaxial with a longitudinal axis and a second bore, the anchoring element has a first end for insertion into the bone and a second end positionable within the second bore and wherein the anchoring element is movable relative to the receiving part in a limited angular range about the longitudinal axis of the receiving part. The anchoring element is pivotable relative to the receiving part around a single rotational axis which is transverse to the longitudinal axis of the receiving part. Hence, the anchoring element is adjustable relative to the receiving part in a single plane.

A bone anchoring device according to the present disclosure combines the features of a monoaxial bone anchoring device and a polyaxial bone anchoring device. It allows a monoplanar adjustment in a single plane, preferably containing the longitudinal axis of the receiving part. The anchoring element is pivotable relative to the receiving part around one axis of rotation which is transverse to the longitudinal axis of the receiving part. Therefore, it is, for example, possible to adjust the position of the receiving part relative to the bone anchoring element only in a single plane. This plane can, for example, extend in parallel to the rod which in use is often the sagittal plane, while a lateral movement in a direction transverse to the rod is prevented. Alternatively, the plane can extend transverse to the rod or in another defined direction. The whole bone anchoring device is more stable therefore.

The receiving part can be shaped like the known receiving parts for the polyaxial bone anchoring devices. Therefore, it is possible to pre-assemble a desired bone anchoring device, either a polyaxial or a monoplanar device according to the actual needs in the surgery, which allows to reduce the costs for stock keeping of the bone anchoring devices.

Further features and advantages of the invention will become apparent and will be best understood by reference to the following detailed description taken in conjunction with the accompanying drawings.

BRIEF DESCRIPTION OF THE DRAWINGS

FIG. 1 shows a perspective exploded view of a bone anchoring device according to an embodiment of the present disclosure.

FIG. 2 shows a sectional view of the bone anchoring device of FIG. 1 in an assembled state in a section along the longitudinal axis of the rod.

FIG. 3 shows a perspective view of the bone anchoring element of the bone anchoring device.

FIG. 4 shows a top view of the bone anchoring element of FIG. 3.

FIG. 5 shows a partial side view of the bone anchoring element of FIG. 3.

FIG. 6 shows a partial side view rotated by 90° of the bone anchoring element of FIG. 3.

FIG. 7 shows a top view of the pressure element of the bone anchoring device.

FIG. 8 shows a side view of the pressure element of the bone anchoring device.

FIG. 9 shows a perspective view of the pressure element of the bone anchoring device from the bottom.

FIG. 10 shows another perspective view of the pressure element of FIG. 9.

FIG. 11 shows a bottom view of the pressure element of the bone anchoring device.

FIG. 12 shows a side view of another embodiment of the pressure element.

FIG. 13 shows a perspective view of the pressure element of FIG. 12.

DETAILED DESCRIPTION

Figure 14A:
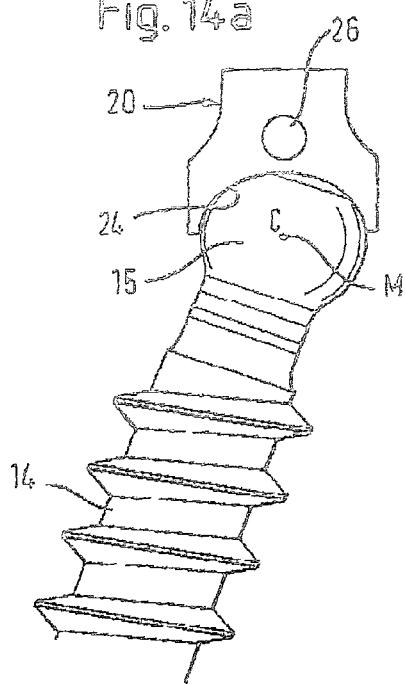
FIGS. 14a) and 14b) show side views of the bone anchoring element together with the pressure element in two different angular positions.

As shown in FIGS. 1 and 2, the bone anchoring device includes a receiving part 1 which is substantially cylindrical and has a first end 2 and a second end 3 opposite to the first end. The two ends extend perpendicular to a longitudinal axis 4. Coaxially with the longitudinal axis 4, a bore 5 is provided which extends from the first end 2 to a predetermined distance from the second end 3. At the second end 3 an opening 6 is provided the diameter of which is smaller than the diameter of the bore 5. The coaxial bore 5 tapers towards the opening 6 in a section 7 which can be for example spherically or conically shaped.

The receiving part 1 further has a U-shaped recess 8 which starts from the first end 2 and extends in the direction of the second end 3 to a predetermined distance from said second end 3. By means of the U-shaped recess 8 two free legs 9, 10 are formed extending towards the first end 2. Adjacent to the first end 2, the receiving part 1 comprises an internal thread 11 on said legs 9, 10. The U-shaped recess 8 serves for receiving a rod 12 by means of which several bone anchoring devices are to be connected.

The bone anchoring device further includes a bone anchoring element 13 comprising a shank 14 with a bone thread and a head 15 at one end. As shown in FIGS. 3 to 6, the head 15 has two sections 16a, 16b which are located opposite to each other and which have a spherical outer surface with the center M of the sphere lying in the center of the head 15. Between the two opposite spherical surfaces 16a, 16b the head 15 comprises two cylindrically-shaped surfaces 17a, 17b with the cylinder axis C being perpendicular to the longitudinal axis L of the bone anchoring element 13 and extending through the center M of the head. On the side opposite to the threaded section 14, the head 15 comprises a flat surface 18. A recess 19 for engagement with screwing-in tool is provided in the flat surface 18. The cylinder radius of the cylindrically-shaped surfaces 17a and 17b is smaller than the radius of the spherical surfaces 16a, 16b. The diameter of the threaded section 14 is smaller than the diameter of the opening 6 of the receiving part so that the anchoring element 13 can be inserted from the first end 2 in the receiving part 1, the threaded section 14 being guided through the lower opening 6 until the spherical surfaces 16a, 16b come into contact with the tapering section 7 of the receiving part 1.

As can be seen from FIGS. 1 and 7 to 15, the bone anchoring device further comprises a pressure element 20 for acting onto the head 15 and to limit a pivoting movement of the head 15 in the receiving part 1. The pressure element 20 is substantially cylindrically shaped and comprises a first end 21 and a second end 22. The outer diameter of the pressure element 20 is slightly smaller than the inner diameter of the bore 5 of the receiving part 1 so that the pressure element 20 can be inserted into the receiving part 1 and can slide within the bore 5. Adjacent to the first end 21 the pressure element 20 includes a cylindrical segment-shaped recess 23 the size of which is such that the rod 12 fits to the recess 23. Adjacent to the second end 22 the pressure element 20 includes a second cylindrical segment-shaped recess 24 the cylinder axis of which is perpendicular to the cylinder axis of the first cylindrical segment-shaped recess 23.

Figure 14B:
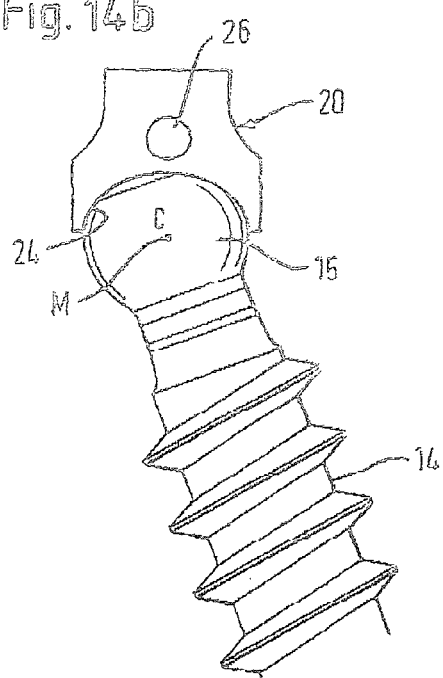
Figure 15:
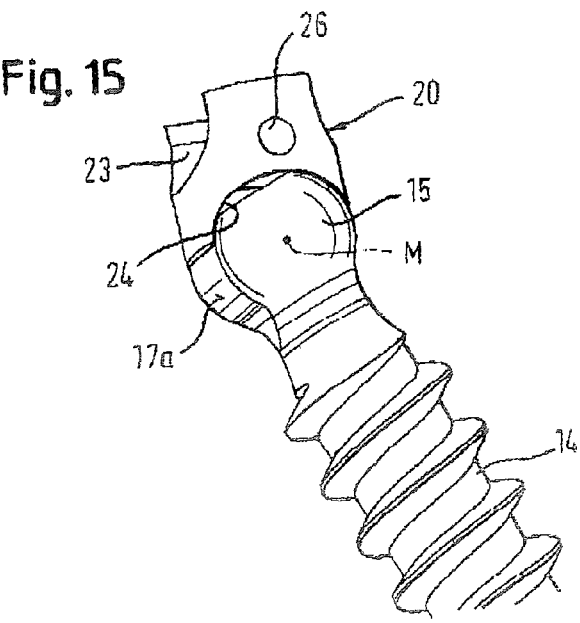
FIG. 15 shows a perspective view of the bone anchoring element together with the pressure element.

The radius of the cylinder segment of the second cylindrical segment-shaped recess 24 corresponds essentially to the radius of the cylindrically-shaped surfaces 17a, 17b of the head 15. The width W of the second cylindrical segment-shaped recess 24 corresponds to the width of the cylindrical surfaces 17a, 17b of the head 15 such that the cylindrical segment-shaped recess 24 covers at least partly the surfaces 17a, 17b when the anchoring element 13 and the pressure element are inserted in the receiving part 1. The pressure element 20 further includes adjacent to the second end 22 two opposite spherical recesses 25a, 25b extending on both sides of the second cylindrical segment-shaped recess 24 and having a diameter which is, for example, equal or larger than the diameter of the opposing spherical surfaces 16a, 16b of the head 15 so that, as can be seen in FIGS. 14a, 14b and 15 the spherical surfaces 16a, 16b of the head 15 are not covered by the pressure element 20.

In addition, the pressure element 20 comprises crimp bores 26 on its outer surface which are located preferably opposite to each other at the sides having the recesses 25a, 25b and which engage with corresponding crimp bores 27 on the legs in the receiving part 1, respectively. The crimp bores 26, 27 serve for a loose pre-assembly of the pressure element 20 within the receiving part so that the pressure element 20 cannot fall out. In this way also the pivoting plane of the anchoring element relative to the receiving part is pre-defined. The pressure element may be secured against rotation in another manner, for example by means of pins or otherwise.

Furthermore, the pressure element 20 has a coaxial bore 28 for allowing access for a screwing-in tool to the recess 19 in the head 15.

In FIGS. 12 and 13 a modified embodiment of the pressure element is shown. The pressure element 20' differs from the pressure element shown in FIGS. 7 to 11 in that the second cylindrical recess 24' is aligned with respect to the first cylindrical recess 23 in such a way that the cylinder axes are parallel. As a result thereof, the axis of rotation for the pivoting motion of the anchoring element is rotated by 90° compared to the case in which the pressure element shown in FIGS. 7 to 11 is used.

As shown in FIGS. 1 and 2 the bone anchoring device also includes an inner screw 30 that can be screwed between the legs 9, 10 to fix the rod 12 and to exert a pressure onto the head 15 via the rod 12.

The whole bone anchoring device can be made of a biocompatible material, for example titanium.

In use, first, the anchoring element 13 is inserted into the receiving part 1 by guiding the threaded shaft 14 through the opening 6 at the second end 3 of the receiving part until the head 15 rests against the section 7 adjacent to the opening 6. Then, the pressure element 20 is inserted into the receiving part 1 with its second end 22 facing the head and is held loosely by the cooperating crimp bores 26, 27 in a position in which the recess 23 of the pressure element is coaxial with the recess 8 of the receiving part 1. The cylindrical surfaces 17a, 17b of the head 15 are covered at least partly with the cylindrical surface of the recess 24 of the pressure element. In this manner pre-assembled, the anchoring element 13 is screwed into the bone.

In this state the anchoring element 13 is still pivotable with respect to the receiving part 1, however, the angular range of pivoting is limited and lies within a plane P which contains the longitudinal axis 4 of the receiving part and forms the plane of mirror symmetry of the receiving part 1. In the embodiment, the plane P is the sectional plane of the section shown in FIG. 2. Pivoting in a single plane is accomplished by the pressure element 20 acting onto the head 15 without exerting pressure onto the head 15 only by the cooperation of the surfaces 17a, 17b with the second cylindrical segment-shaped recess 24 which allows a pivoting motion around the cylinder axis C but prevents pivoting in another direction. Therefore, an adjustment of the position of the receiving part with respect to the anchoring element 13 in the sagittal plane, i.e., along the rod 12 when the device is in use, is possible, whereas an adjustment in a lateral direction, i.e., transverse to the rod 12 when the device is in use, is blocked. After adjustment of the position of the receiving part 1 the rod 12 is inserted and an inner screw 30 is screwed-in between the legs 9, 10 and tightened to exert a pressure onto the rod which itself exerts a pressure onto the pressure element 20. The pressure element 20 then exerts a pressure onto the head 15 to lock it in its final position. Hence, the rotation of the anchoring element 13 around the longitudinal axis 4 is prevented by the form-fit cooperation of the cylindrical surfaces of the head 15 and the pressure element whereas the locking of the angular motion of the head in the single plane is achieved by frictional forces acting between the head 15 and the pressure element 20.

Figure 16:
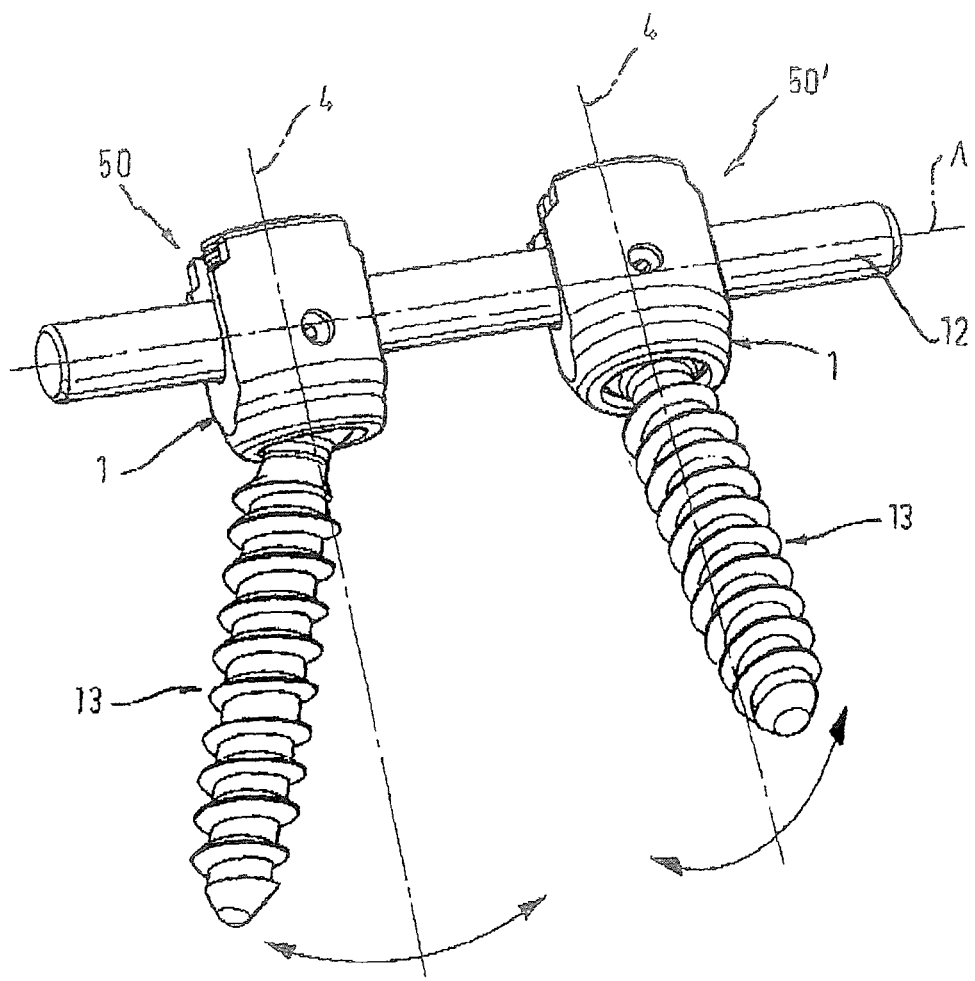
FIG. 16 shows two bone anchoring elements according to the invention together with a rod.
Figure 17:
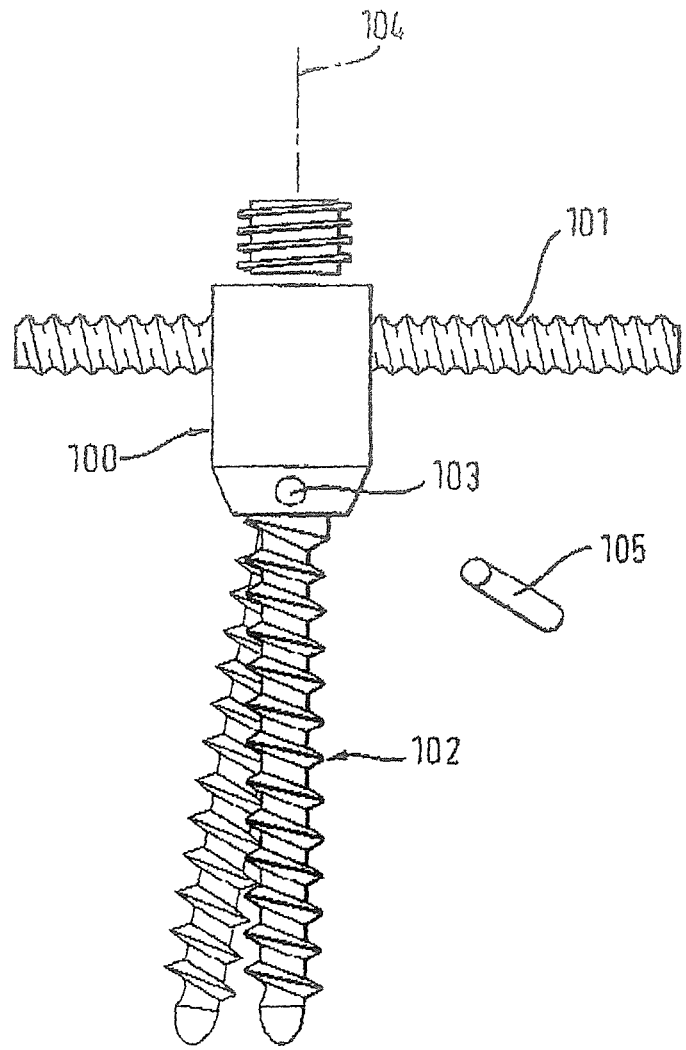
FIG. 17 shows the known cosmic posterior dynamic system.

In FIG. 16 two bone anchoring devices 50, 50' are shown which are connected by a rod 12. The first bone anchoring device 1 comprises the pressure element 20 shown in FIGS. 7 to 11. The axis of rotation of the anchoring element 13 is perpendicular to the rod axis A which allows an adjustment in a plane defined by the longitudinal axis 4 of the receiving part 1 and the rod axis A. The second bone anchoring element 50' comprises a pressure element 20' as shown in FIGS. 12 and 13. The axis of rotation of the bone anchoring element 13 is parallel to the rod axis A which allows an adjustment of the anchoring element 13 in a single plane which is perpendicular to the rod axis A and includes the longitudinal axis 4 of the receiving part.

The alternative embodiments of pressure elements 20,20' as shown in FIG. 16 may simultaneously be employed with regard to the two bone anchoring devices 50, 50' connected by the same rod 12. In accordance with one embodiment of the present disclosure, each bone anchoring device 50,50' can be associated with two pressure elements 20,20' so as to provide interchangeable use of the pressure elements 20,20'. Referring to FIG. 16, the bone anchoring device 50 with the pressure element 20 enables a rotation of the anchoring element 13 in a sagittal plane. When the pressure element 20' is used with the bone anchoring device 50, however, a rotation of the anchoring element 13 in a transversal plane is enabled. Similarly, the bone anchoring device 50' with the pressure element 20' enables a rotation of the anchoring element 13 in a transversal plane. When the pressure element 20 is used with the bone anchoring device 50', however, a rotation of the bone anchoring element 13 in a sagittal plane is enabled. Accordingly, the interchangeable use of the pressure elements 20,20' with each bone anchoring device 50 or 50' can provide a surgeon with the ability to select any one of the sagittal and transversal planes of motion for any anchoring device 50 or 50'. One of ordinary skill in the art will appreciate that a number of additional interchangeable pressure elements can be provided so that each additional pressure element enables a plane of rotation other than sagittal or transversal planes as described above. Thus, with the ability to interchangeably use the pressure elements 20, 20' and/or any additional pressure elements enabling different planes of rotation for the anchoring element 13, a surgeon has the freedom to choose a pressure element depending on the requirements of each situation.

As can be seen from FIGS. 14a, 14b, 15 and 16 the bone anchoring device according to the disclosure allows an adjustment in a single plane or, in other words, a rotation around one rotational axis. Therefore, the anchoring element is connected to the receiving part in a monoplanar manner. The bone anchoring device is more stable than a polyaxial bone anchoring device which allows a pivoting in a range of 360° around the longitudinal axis. It has an improved resistance to loads and allows a positional adjustment of the receiving part which is sufficient for specific clinical applications. By selecting the appropriate pressure element it is possible to assemble a bone anchoring device which can be adjusted in a desired plane relative to the rod according to the actual anatomical requirements.

The bone anchoring device is not limited to the embodiments discussed above. Modifications are conceivable. Any orientation of the two cylinder axes of the first and the second cylindrical recesses of the pressure element with respect to each other is possible. The cylinder segment-shaped recess 23 of the pressure element can be omitted. That means, the first end 21 of the pressure element can have a flat surface. In this case, the pressure element can be oriented within the receiving part such that the second cylinder segment-shaped recess is aligned in any desired direction.

The surfaces 16a, 16b of the head 15 do not need to have a spherical shape. They can also be flat.

The single plane in which the anchoring element can be pivoted must not include the longitudinal axis. It can also extend in parallel to the longitudinal axis.

The receiving part can have an asymmetric edge at the opening 6 to enable a larger pivot angle on one side of the longitudinal axis that on the other side. The asymmetry in the pivot angle can be achieved also by other means.

In the embodiment shown the pressure is exerted via the rod 12 onto the pressure element 20 which itself presses onto the head. It is, however, possible to separate the locking of the head 15 via the pressure element 20 from the locking of the rod 12. For this purpose, the recess 23 in the pressure element 20 comprises upwardly extending legs extending above the inserted rod 12 so that it is possible to press separately onto these legs via separate inner screw encompassing the inner screw 30 which presses onto the rod.

In a further modification, a construction is possible in which the head is inserted into the receiving part 1 from the second end 3. In this case the opening 6 must be large enough to introduce the head and means must be provided to prevent falling-out of the head.

In another modification the lower opening 6 of the receiving part is provided with a thread which cooperates with the thread of the shaft 14 of the anchoring element. In this case the threaded shaft 14 of the anchoring element 13 can be screwed-in the opening and further into the bone. The diameter of the threaded shaft can be as large as the diameter of the first bore 5.

Instead of the threaded shaft 14 any other bone anchoring means is conceivable, such as nails or hooks.

The bone anchoring device needs not to be pre-assembled before use in surgery. It can also be assembled during surgery.

What is claimed is:

1. A bone anchoring device comprising:
    a receiving part for receiving a rod, the receiving part having a longitudinal axis, a first end and a second end, the receiving part further having a first bore coaxial with the longitudinal axis and extending from the first end to an opening at the second end, the opening is smaller than the bore and the first bore tapers toward the opening in a tapered section that forms a seat;
    an anchoring element having a first end for insertion into the bone and a second end, the second end including a head that is positionable against the seat, the anchoring element being movable relative to the receiving part in a limited angular range about the longitudinal axis, the angular range lying in a single plane; and
    a fixation element cooperating with the receiving part to lock the anchoring element relative to the receiving part; and
    a pressure element configured to lock an angular position of the anchoring element with respect to said receiving part, the pressure element having two legs extending toward the seat of the receiving part and terminating in the bore at the start or before the tapered section when assembled and locked in place;
    wherein movement of the anchoring element before locking is limited to the single plane by a form-fit connection between the head of the anchoring element and the pressure element.

2. The bone anchoring device of claim 1, wherein the single plane includes the longitudinal axis.

3. The bone anchoring device of claim 1, wherein the angular range is symmetrical about the longitudinal axis.

4. The bone anchoring device of claim 1, wherein the head is pivotable in the receiving part in the single plane.

5. The bone anchoring device of claim 1, wherein the head is mirror symmetrical and has a guiding surface cooperating with a matching guiding surface located within the pressure element.

6. The bone anchoring device of claim 5, wherein said guiding surfaces of the head and the pressure element are cylindrically shaped and have a common axis, the common axis being perpendicular to the longitudinal axis of the receiving part.

7. The bone anchoring device of claim 1, wherein the locking of the angular motion of the anchoring element in the receiving part is achieved by frictional forces.

8. The bone anchoring device of claim 1, wherein an inner surface of the receiving part is substantially symmetric with respect to rotation around the longitudinal axis.

9. The bone anchoring device of claim 1, wherein the head of the anchoring element has a spherical segment shaped portion with a spherical center, and wherein when the pressure element is assembled and locked in place, the spherical center of the head is closer than ends of the two legs of the pressure element to the second end of the receiving part along the longitudinal axis.

10. A bone anchoring device comprising:
    a receiving part for receiving a rod, the receiving part having a longitudinal axis, a first end and a second end, the receiving part further having a first bore coaxial with the longitudinal axis and extending from the first end to an opening at the second end, the opening is smaller than the bore and the first bore tapers toward the opening in a tapered section that forms a seat;
    an anchoring element having a first end for insertion into the bone and a second end, the second end including a head that is positionable against the seat;
    a pressure element configured to provide pivotable coupling of the anchoring element relative to the receiving part around a single axis of rotation which is transverse to the longitudinal axis of the receiving part and to lock an angular position of the anchoring element with respect to the receiving part, the pressure element having two legs extending toward the seat of the receiving part and terminating in the bore at the start of or before the tapered section when assembled and locked in place; and
    a fixation element cooperating with the receiving part to lock the anchoring element relative to the receiving part.

11. The bone anchoring device of claim 10, wherein the pivoting of the anchoring element relative to the receiving part is symmetrical about the longitudinal axis.

12. The bone anchoring device of claim 10, wherein the head is mirror symmetrical and has a guiding surface cooperating with a matching guiding surface located within the pressure element.

13. The bone anchoring device of claim 12, wherein said guiding surfaces of the head and the pressure element are cylindrically shaped and have a common axis, the common axis of the guiding surfaces being the single axis of rotation.

14. The bone anchoring device of claim 10, wherein the locking of the anchoring element in the receiving part is achieved by frictional forces.

15. A bone anchoring device comprising:
    a receiving part for receiving a rod, the receiving part having a longitudinal axis, a first end and a second end, the receiving part further having a first bore coaxial with the longitudinal axis and extending from the first end to an opening at the second end, the opening is smaller than the bore and the first bore tapers toward the opening in a tapered section that forms a seat;
    an anchoring element having a first end for insertion into the bone and a second end, the second end including a head that is positionable against the seat;

a first pressure element configured to couple to the head in the receiving part to provide pivoting of the head relative to the receiving part in a first angular range, the first angular range lying in a first plane, the pivoting of the head being limited to the first angular range by a form-fit coupling between the head and the first pressure element, and to lock an angular position of the anchoring element with respect to the receiving part;

a second pressure element configured to couple to the head in the receiving part to provide pivoting of the head relative to the receiving part in a second angular range, the second angular range lying in a second plane, the pivoting of the head being limited to the second angular range by a form-fit coupling between the head and the second pressure element, and to lock the angular position of the anchoring element with respect to the receiving part; and a fixation element cooperating with the receiving part to lock the pivoting of the anchoring element relative to the receiving part;

wherein each of the first and second pressure elements has two legs, and wherein the first pressure element and the second pressure element are interchangeable to provide pivoting of the head in the first plane and in the second plane, respectively, such that when the first or second pressure element is assembled and locked in place in the receiving part, the two legs of the assembled and locked pressure element extend toward the seat of the receiving part and terminate in the bore at the start of or before the tapered section.

16. The bone anchoring device of claim 15, wherein the first plane is perpendicular to the second plane.

17. The bone anchoring device of claim 15, wherein the longitudinal axis lies in the first plane and the second plane.

18. The bone anchoring device of claim 15, wherein the first angular range and the second angular range are symmetrical about the longitudinal axis.

19. The bone anchoring device of claim 15, wherein the head is mirror symmetrical and has a guiding surface configured to cooperate with a matching guiding surface located within the first pressure element and a matching guiding surface located within the second pressure element.

20. The bone anchoring device of claim 19, wherein said guiding surfaces of the first pressure element, the second pressure element and the head are cylindrically shaped, wherein the guiding surface of the head and the first pressure element have a first common axis when the head is coupled to the first pressure element, the first common axis being perpendicular to the longitudinal axis of the receiving part, and wherein the guiding surface of the head and the second pressure element have a second common axis when the head is coupled to the second pressure element, the second common axis being perpendicular to the longitudinal axis of the receiving part.

21. The bone anchoring device of claim 15, wherein the locking of the angular motion of the anchoring element in the receiving part is achieved by frictional forces.

22. A bone anchoring device comprising:
a receiving part for receiving a rod, the receiving part having a longitudinal axis, a first end and a second end, the receiving part further having a first bore coaxial with the longitudinal axis and extending from the first end to an opening at the second end, the opening is smaller than the bore and the first bore tapers toward the opening in a tapered section that forms a seat;

an anchoring element having a first end for insertion into the bone and a second end positionable within a second bore, the second end including a head, the anchoring element being movable relative to the receiving part in a limited angular range about the longitudinal axis, the angular range lying in a single plane; and a fixation element cooperating with the receiving part to lock the anchoring element relative to the receiving part;

wherein the head of the anchoring element has two sections located opposite to each other and which each have an outer surface configured to engage the seat of the receiving part;

wherein between and on each side of the outer surfaces, the head further has two cylindrically-shaped surfaces located opposite each other and having a cylindrical axis that extends from one of the two outer surfaces to the other of the two outer surfaces.

* * * * *

UNITED STATES PATENT AND TRADEMARK OFFICE
CERTIFICATE OF CORRECTION

Page 1 of 1

PATENT NO.         : 8,506,611 B2
APPLICATION NO.    : 13/245361
DATED              : August 13, 2013
INVENTOR(S)        : Lutz Biedermann et al.

It is certified that error appears in the above-identified patent and that said Letters Patent is hereby corrected as shown below:

On the Title Page

Item (63) Related U.S.　　　　　Delete "8,048,183"
Application Data, line 2　　　　Insert -- 8,048,133 --

In the Claims

Column 7, line 52, Claim 1　　　After "start"
　　　　　　　　　　　　　　　Insert -- of --

Signed and Sealed this
Second Day of December, 2014

Michelle K. Lee
*Deputy Director of the United States Patent and Trademark Office*